(12) United States Patent
Ohtsu

(10) Patent No.: US 7,094,947 B2
(45) Date of Patent: Aug. 22, 2006

(54) ANIMALS WITH HIGH HISTAMINE PRODUCTIVITY

(75) Inventor: Hiroshi Ohtsu, Miyagi (JP)

(73) Assignee: Japan Science and Technology Corporation, Saitama (JP)

( * ) Notice: Subject to any disclaimer, the term of this patent is extended or adjusted under 35 U.S.C. 154(b) by 144 days.

(21) Appl. No.: 10/239,223

(22) PCT Filed: Mar. 23, 2001

(86) PCT No.: PCT/JP01/02363

§ 371 (c)(1),
(2), (4) Date: Oct. 25, 2002

(87) PCT Pub. No.: WO01/70016

PCT Pub. Date: Sep. 27, 2001

(65) Prior Publication Data
US 2005/0005315 A1    Jan. 6, 2005

(30) Foreign Application Priority Data
Mar. 23, 2000    (JP)    ............................. 2000-082953

(51) Int. Cl.
*A01K 67/00*    (2006.01)
*A01K 67/027*    (2006.01)
*C07H 21/04*    (2006.01)

(52) U.S. Cl. ........................ 800/18; 800/13; 536/23.5; 536/24.1

(58) Field of Classification Search .................. 800/13, 800/14, 18; 536/23.5, 24.1
See application file for complete search history.

(56) References Cited

OTHER PUBLICATIONS

Kappel et al., 1992, Current Opinion in Biotechnology, vol. 3, p. 548-553.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
Yamauchi et al., 1993, Advances in the Biosciences, vol. 89, p. 177-196.*
D. R. Joseph et al., Proc. Natl. Acad. Sci., USA, vol. 87, pp. 733-737, 1990.
S. Ishizaki et al., Japan J. Pharmacol., vol. 82, Suppl. 1, p. 113, Mar. 1, 2000.
H. Nagai et al., Japan Pharmacol. Exp. Therap., vol. 288, pp. 43-50, 1990.
H. M. Kim et al., Immunology, vol. 96, pp. 551-556, 1999.
T. Watanabe et al., Folia. Pharmacol. Japan, vol. 106, Suppl. 1, pp. 14-19, 1995.

* cited by examiner

*Primary Examiner*—Shin-Lin Chen
(74) *Attorney, Agent, or Firm*—Wenderoth, Lind & Ponack, L.L.P.

(57) ABSTRACT

The invention of the present patent application provides, a histamine-hyperproductive animal, which is a non-human animal or progeny thereof obtained by ontogenesis of totipotent cell transfected with a polynucleotide encoding histidine decarboxylase and has the above polynucleotide in the cellular chromosome to produce histamine at a high level in the somatic cells. Thus, analysis of the pathogenesis and pathological consequence in various disorders associated with histamine in human as well as development of therapeutic techniques and remedies for these disorders will be developed.

1 Claim, 3 Drawing Sheets

ANIMALS WITH HIGH HISTAMINE PRODUCTIVITY

This is a 371 U.S. National Stage Application of PCT/JP01/02363, filed Mar. 23, 2001.

TECHNICAL FIELD

The invention of the present application relates to a histamine-hyperproductive animal. More particularly, it relates to a transgenic animal in which an exogenous gene for histamine synthetase has been introduced into the somatic chromosome, whereby the animal is capable of producing histamine in excess in their body.

BACKGROUND ART

Histamine is a member of autacoids acting in the living body, abundant in the skin, lung, digestive organs, and so on, which is released in allergy and anaphylaxis and associated with the onset of urticaria or inflammation or hematopoiesis. In the gastric mucosa, it has been found that histamine is involved in the generation of gastric ulcers because it is present in the enterochromaffin cells to play an important role in promoting secretion of gastric juice.

Thus, since histamine is involved in a variety of human disorders and alteration of physical condition, elucidation of the mechanism of its action is essential for development of the therapeutics and remedies used in histamine-related diseases. Since these diseases or change of physical condition arise in the context of i various tissues or organs in the body, it is indispensable to study the effect of histamine in vivo using a model animal.

In this viewpoint, the inventors of the present application have already invented knockout animals (animals lackng in histamine) in which th gene for histamine synthetase has been knocked out, and filed as the Japanese Patent Application no. 11-246315 (1999). However, animals expressing histamine in excess have not yet been known.

Therefore, it has eagerly been desired to develop a model animal system by which a variety of symptoms in animal individuals in the excess state of histamine could be analyzed systematically. It has also been expected that such model animals might be a powerful tool for developing remedies used in treatment of a variety of disorders associated with histamine.

The invention was made in view of the above-mentioned situation, aiming for providing animals with high histamine productivity, capable of producing histamine in excess in the body.

DISCLOSURE OF INVENTION

The present patent application provides, as an invention for solving the above-mentioned problems, a histamine-hyperproductive animal, which is a non-human animal or progeny thereof obtained by ontogenesis of totipotent cells transfected with a polynucleotide encoding histidine decarboxylase and which has the above polynucleotide in the cellular chromosome to produce histamine at a higher level in the somatic cells.

According to a preferred embodiment of the invention, the non-human animals are mice.

BEST MODE FOR CARRYING OUT THE INVENTION

Figure 1:
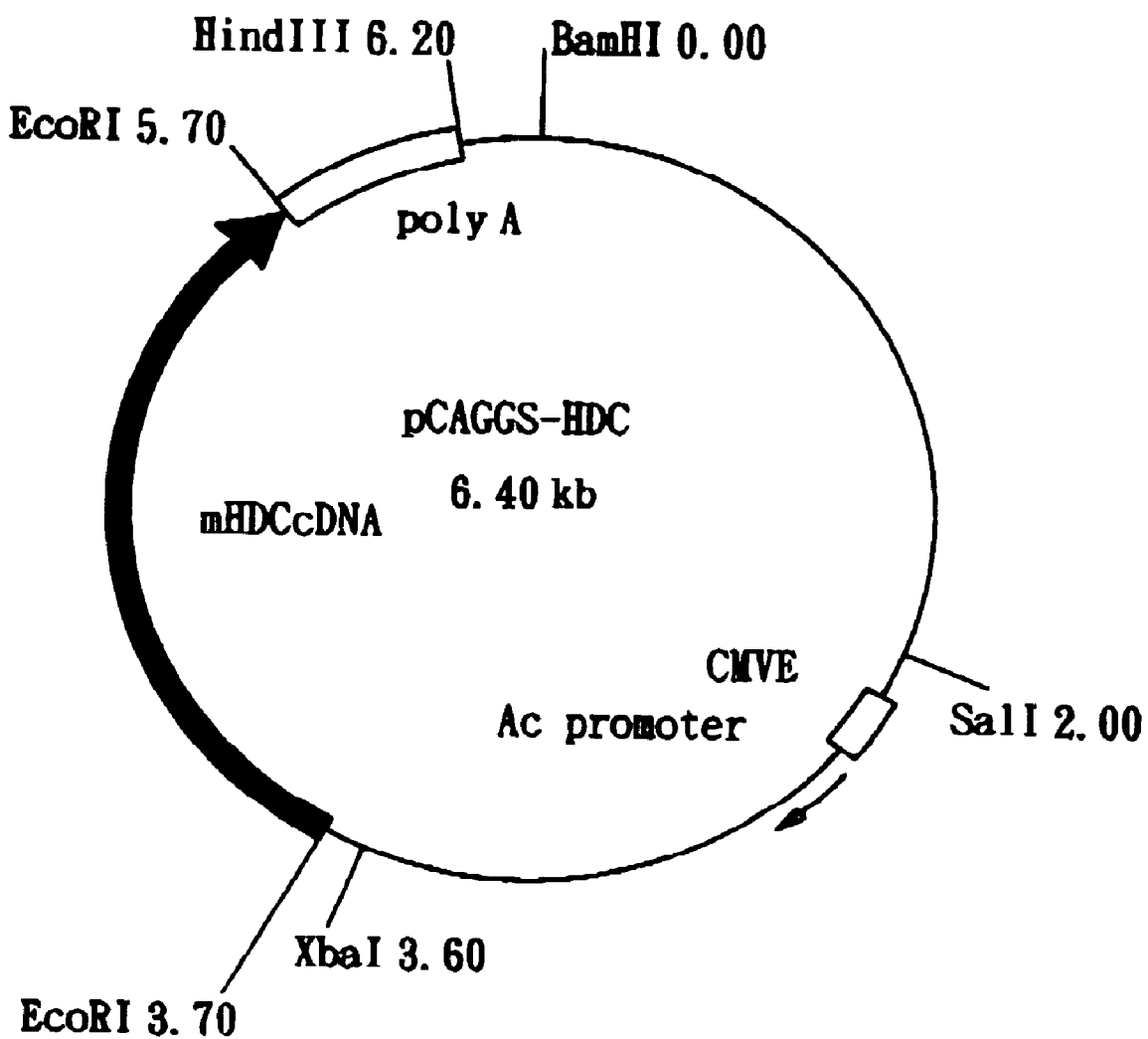
FIG. 1 is a diagrammatic illustration of the structure of a transgenic vector used in Examples.

The transgenic animals of the invention can be generated according to the known method for generating transgenic animals (for example, Proc. Natl. Acad. Sci. USA, 77: 7380–7384, 1980). That is, a polynucleotide coding for L-histidine decarboxylase (HDC)(hereinafter sometimes referred to as "transgene") is transferred into totipotent cells of a non-human animal, which are induced to ontogeny, and the individuals in which the transgene has been integrated in the somatic cells are screened to obtain the intended transgenic animals. Concerning the non-human animals, though all kinds of animals can be used technically as targets, mice are most preferred because a large number of inbred strains have been generated and also established technology for cultivation of fertilized eggs and for external fertilization have been existed.

The transgene is a DNA fragment including a polynucleotide coding for HDC. Such a polynucleotide may be derived from the known cDNA of murine HDC (FEBS Lett., 276: 214–218, 1990) or from the CDNA of rat HDC (Pro. Natl. Acad. Sci. USA, 87: 733–737, 1990). Alternatively, it is also possible to obtain the HDC cDNA derived from other animals by screening cDNA libraries of those animals with an oligonucleotide probe synthesized based on the murine or rat cDNA or by RT-PCR using olinucleotide primes. In order to control the expresson, a promoter sequence and an enhancer sequence are ligated to the transgene. Depending on selection of the promoter/enhancer sequence, it is possible to a HDC systemically or in a specific tissue.

Such a transgene may be constructed by insertion and ligation of the above mentioned polynucleotide and promoter/enhancer sequences into a cyclic vector DNA, a plasmid, so that they are located properly for effective control of the transgene expression. And the vector DNA is cleaved to give a linear fragment, which is then transferred into totipotent cells.

As for the totipotent cells into which a gene is transferred, in case of mice, fertilized eggs or early embryos may be used. As a method for gene transfer, it is most appropriate to use a physical injection (micro-injection) methodin point of the efficiency of generation of the individual transgenic animals and of transfer of the transgene to the next generation.

The gene-injected fertilized eggs are then implanted into the oviduct of pseudo-pregnant mothers to mature and fed with a foster parent post partum. Subsequently, DNAs are extracted from a part of the body (in case of a mouse, from the tail) to confirm the presence of the transgene by the Southern analysis or PCR. Once the transgene has been confined in the mouse, they are defined as a founder and it will be transmitted to the next generation (F2) at a rate of 50%. Further, the F1 individual can be mated with a wild type or another F1 individual to yield a new individual (F2) in which the transgene has been transferred into one (heterozygote) or both (homozygote) allele(s) of the diploid chromosomes.

Thus the transgenic animals generated here are expressing the exogenous HDC in excess in all of the somatic cells or a specific tissue, resulting in production of histamine at a high level.

The transgenic animals thus produce histamine at a high level, thereby developing a variety of disorders (allergy and gastric ulcer) caused by histamine. Therefore, they are useful as animal models in order to develop remedies or therapeutics in treatment of such disorders.

The invention will be better explained in details and specifically by the following examples, but which are not intended as a limitation thereof.

EXAMPLES

Example 1

Generation of Mice with High Histamine Productivity

Using an oligonucleotide probe which was synthesized based on the cDNA sequence of murine HDC (FEBS Lett.276:214–218,1990), a murine CDNA library was screened for the murine HDC cDNA. This cDNA was inserted into a plasmid vector "pCAGGS" to construct a transgene pCAGGS-HDC (FIG. 1). In this vector, the HDC cDNA is positioned under the control of the chicken gamma-actin promoter so that it is expressed in various tissues of the transgenic mice.

The vector was digested with restriction enzymes, SalI and HindIII, to eliminate the vector backbone. The resulting linear fragment was injected into the pronuclei of fertilizd eggs of BDF1 mice by a microinjection method. The gene transferred fertilized eggs were then implanted into the oviduct of pseudo-pregnant mother in a conventional way to grow to individuals.

Figure 2:
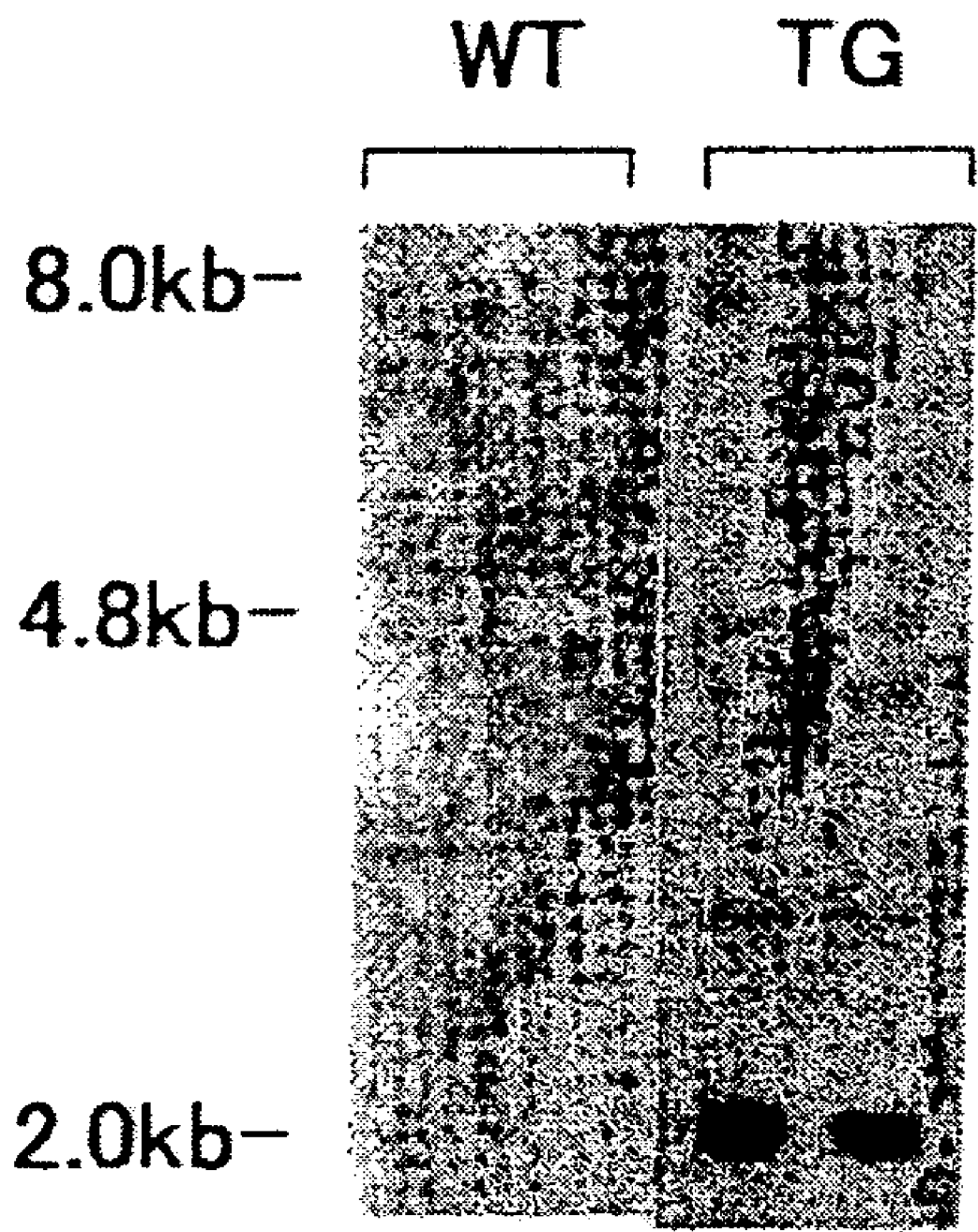
FIG. 2 shows the result of confirmation by the Southern blot analysis of the presence of the transgene.

From the tail of the resulting mouse individual, gmnomic DNA was extracted and digested with EcoRI. Then, the transgenic mice were screened according to the conventional Southern analytical method using an oligonucleotide as a probe consisting of a partial sequence of murine HDC cDNA. FIG. 2 shows the results. In wild-type (WT) mice, endogenous HDC fragments (about 8.0 kb, 4.8 kb) were detected, while the transferred HDC fragment of about 2.0 kb was detected in addition to these endogenous gene fragments in the transgenic mice (TG). From the above results, it was confirmed that the mice No. 641 and 642 were trasgenic mice with the transgene on the chromosome.

Figure 3:
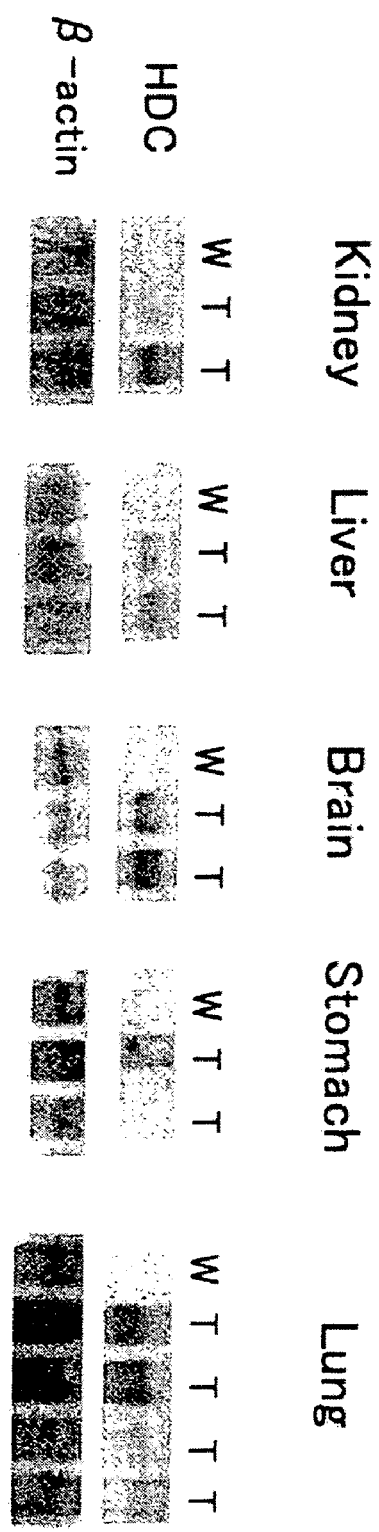
FIG. 3 shows the result of confirmation of expression of the transgene by the Northern blot analysis of the tissues.

In addition, expression of the transgene in these transgenic mice was examined in their tissue by the Northern analysis. As seen in FIG. 3, excessive expression of the transfered HDC gene was observed in almost all the tissues (kidney, liver, brain, stomach, and lung) examined in the transgenic mouse (T)

Example 2

Determination of the Amount of Histamine in the Transgenic Mice

The amount of histamine and the HDC activity were determined in several organs (cerebral cortex, midbrain, kidney, and stomach) of the transgenic mice generated in Example 1 as well as wild-type mice (Nos. 646 and 647).

The amount of histamine was determined in accordance with the known combined method consisting of high performance liquid chromatography and fluorometry (J. Chromatogr. 344: 115–123, 1985). Briefly, respective tissues were homogenized with a homogenizer, then treated with perchloric acid, and then centrifuged. An aliquot of the supernatant was separated by high performance liquid chromatography, and allowed to react with a fluorescent dye o-phthalaldehyde under alkaline conditions to determine the amount of histamine from the fluorescence intensity of the reaction product as an indicator.

The HDC activity was determined by means of the amount of histamine from histidine as substrate based on the known method (J. Biochem. 107; 834–839, 1990). Briefly, respective tissues were sonicated in a buffer solution for the HDC reaction. The sonicated sample was centrifuged, and the supernatant was separated and dialyzed overnight against the buffer solution for the HDC reaction. After dialysis, L-histidie as substrate was added and allowed to react at 37° C. for 2 hours. The produced histimine was measured according to the above method to determine the activity of HDC.

The results are shown in Table 1 (HDC activity) and Table 2 (the amount of histamine). In all of the organs examined, the HDC activity (in Table 1, HDC act. and the average values AVG) and the amount of histamine (in Table 2, pmol/g and the average values AVG) both were increaed in the transgenic mice compared with those of the wild-type mice. From these results, it was confirmed that the HDC transgenic mice generated in Example 1 were mice with high histamine productivity.

TABLE 1

|  |  | Histidine+ | Histidine− | (+ − −) | mg prot. | HDC act. | AVG | TG/wild |
|---|---|---|---|---|---|---|---|---|
| 641 | cortex | 640.4734 | 6.521087 | 646.9945 | 0.5103 | 10.56559 | 5.927722 | 20.79827 |
| 642 | cortex | 76.91173 | 2.708377 | 79.6201 | 0.5144 | 1.289854 | | |
| 646 | cortex | 18.19627 | 1.402746 | 19.59902 | 0.51145 | 0.319337 | 0.28501 | |
| 647 | cortex | 9.672152 | 2.046287 | 11.71844 | 0.38955 | 0.250683 | | |
| 641 | mid. | 225.595 | 2.007538 | 227.6026 | 0.27435 | 6.913389 | 6.358457 | 17.59877 |
| 642 | mid. | 189.3318 | 1.488071 | 190.8199 | 0.274 | 5.803525 | | |
| 646 | mid. | 9.147402 | 1.345798 | 10.4932 | 0.2445 | 0.357641 | 0.361301 | |
| 647 | mid. | 9.336193 | 2.116288 | 11.45248 | 0.2615 | 0.364961 | | |
| 641 | kidney | 2227.092 | 457.7291 | 2684.821 | 1.2995 | 17.21701 | 14.82442 | 0.977838 |
| 642 | kidney | 1703.095 | 382.4702 | 2085.565 | 1.398 | 12.43184 | | |
| 646 | kidney | 1997.341 | 499.9867 | 2497.327 | 1.1965 | 17.39328 | 15.16041 | |
| 647 | kidney | 1635.964 | 213.1143 | 1849.078 | 1.19195 | 12.92754 | | |
| 641 | st. | 1320.89 | 15.10884 | 1335.999 | 0.5609 | 19.84904 | 17.79592 | 30.04573 |
| 642 | st. | 850.4966 | 7.454651 | 857.9513 | 0.45415 | 15.7428 | | |

TABLE 1-continued

|  | Histidine+ | Histidine− | (+ − −) | mg prot. | HDC act. | AVG | TG/wild |
|---|---|---|---|---|---|---|---|
| 646 st. | 22.22755 | 0 | 22.22755 | 0.4385 | 0.422416 | 0.592294 | |
| 647 st. | 40.06894 | 0 | 40.06894 | 0.4381 | 0.762173 | | |

TABLE 2

| Sample | Area | pmol/ml | g | pmol/g | AVG | TG/Wild |
|---|---|---|---|---|---|---|
| Cort-641 | 2960809 | 536.2428 | 0.20726 | 2587.295 | 1908.832 | 7.463778 |
| Cort-642 | 1436794 | 260.2229 | 0.2115 | 1230.368 | | |
| Cort-646 | 153844 | 27.86324 | 0.2039 | 136.6515 | 255.746 | |
| Cort-647 | 342526 | 62.03612 | 0.1655 | 374.8406 | | |
| Mid-641 | 2033368 | 368.2706 | 0.12566 | 2930.691 | 2334.818 | 8.820128 |
| Mid-642 | 967822 | 175.2857 | 0.1008 | 1738.946 | | |
| Mid-646 | 130723 | 22.66251 | 0.0939 | 241.3472 | 264.7148 | |
| Mid-647 | 194921 | 33.79205 | 0.1173 | 288.0823 | | |
| Kid-641 | 46432775 | 8049.716 | 0.2889 | 27863.33 | 27671.44 | 2.137994 |
| Kid-642 | 68428289 | 11862.92 | 0.4317 | 27479.55 | | |
| Kid-646 | 27439878 | 4757.054 | 0.2845 | 16720.75 | 12942.71 | |
| Kid-647 | 14162296 | 2455.215 | 0.2679 | 9164.671 | | |
| Stom-641 | 35450278 | 6420.527 | 0.14365 | 44695.63 | 40493.66 | 1.335019 |
| Stom-642 | 44063738 | 7980.542 | 0.2199 | 36291.69 | | |
| Stom-646 | 40388951 | 7314.988 | 0.2175 | 33632.13 | 30331.9 | |
| Stom-647 | 18775969 | 3400.583 | 0.1258 | 27031.66 | | |

INDUSTRIAL APPLICABILITY

According to the invention, as described in detail, a histamine-hyperproductve animal having a foreign HDC gene in chromosome is rovided. With this animal, asks of the pathogenesis and pathological consequence in various disorder associated with histamine in human as well as development of therapeutic techniques and remedies for these disorders will be developed.

What is claimed is:

1. A transgenic mouse whose genome comprises an exogenous polynucleotide encoding a histidine decarboxylase under the control of a promoter, wherein said transgenic mouse produces significantly higher level of histamine in cerebral cortex and mid-brain as compared to a wild-type mouse.

\* \* \* \* \*